United States Patent
Eisele et al.

[11] Patent Number: 5,622,166
[45] Date of Patent: Apr. 22, 1997

[54] DRY POWDER INHALER DELIVERY SYSTEM

[75] Inventors: Robert F. Eisele, Laguna Niguel; Allan Cameron, Santa Monica; David Titzler, Newbury Park; Leonard Porche, Simi Valley, all of Calif.

[73] Assignee: Dura Pharmaceuticals, Inc., San Diego, Calif.

[21] Appl. No.: 428,960

[22] Filed: Apr. 24, 1995

[51] Int. Cl.$^6$ .................................................. A61M 15/00
[52] U.S. Cl. .............................. 128/203.12; 128/203.15; 128/203.21
[58] Field of Search ................................ 206/531, 532; 128/203.15, 203.21, 203.12, 200.14

[56] References Cited

U.S. PATENT DOCUMENTS

| | | | |
|---|---|---|---|
| 3,327,843 | 6/1967 | O'Meara et al. | 206/532 |
| 3,759,371 | 9/1973 | Marks | 206/531 |
| 3,948,394 | 4/1976 | Hellstrom | 206/531 |
| 4,294,361 | 10/1981 | Margulies et al. | 206/532 |
| 4,627,432 | 12/1986 | Newell et al. | 128/203.15 |
| 4,778,054 | 10/1988 | Newell et al. | 206/531 |
| 4,811,731 | 3/1989 | Newell et al. | 128/203.15 |
| 4,971,221 | 11/1990 | Urquhart et al. | 221/2 |
| 5,019,125 | 5/1991 | Rebne et al. | 206/531 |
| 5,035,237 | 7/1991 | Newell et al. | 128/203.15 |
| 5,042,472 | 8/1991 | Bunin | 128/203.15 |
| 5,172,812 | 12/1992 | Wharton et al. | 206/531 |
| 5,207,217 | 5/1993 | Cocozza et al. | 128/203.21 |
| 5,239,991 | 8/1993 | Chawla et al. | 128/203.15 |
| 5,349,947 | 9/1994 | Newhouse et al. | 128/203.21 |

FOREIGN PATENT DOCUMENTS

| | | |
|---|---|---|
| 0129985 | 5/1984 | European Pat. Off. |
| 0118179 | 9/1984 | European Pat. Off. |
| 0469814 | 7/1991 | European Pat. Off. |
| 2638430 | 10/1988 | France . |
| 2142246 | 1/1985 | United Kingdom . |
| 2242134 | 1/1991 | United Kingdom . |
| 9106333 | 5/1991 | WIPO . |
| 9200771 | 1/1992 | WIPO . |
| 9204069 | 3/1992 | WIPO . |
| 9408552 | 4/1994 | WIPO . |
| 9420164 | 9/1994 | WIPO . |
| 9427653 | 12/1994 | WIPO . |

*Primary Examiner*—Aaron J. Lewis
*Attorney, Agent, or Firm*—Lyon & Lyon

[57] ABSTRACT

A powder storage and delivery system for a drug powder inhaler has a carrier disk with a blister shell sealed by a shear layer. A tab is adhered to the shear layer, underneath the blister shell. The carrier disk is placed into a dry powder inhaler. An actuator pushes against the tab, causing the shear layer to tear away, releasing the powder drug contents from the blister into the dry powder inhaler. A disk carrier has bursting blisters with a brittle blister shell sealed with a foil lid, and covered by a plate. An actuator moves against the plate, causing the plate to buckle and the blister shell to burst open, releasing powdered drug into the dry powder inhaler.

26 Claims, 7 Drawing Sheets

5,622,166

DRY POWDER INHALER DELIVERY SYSTEM

BACKGROUND OF THE INVENTION

Field of the Invention

The field of the invention is dry powder storage devices and systems for powdered drugs.

Various drugs in a dry powder mixture form may be inhaled directly into the lungs, through the mouth or nose. Inhalation allows the drug to bypass the digestive system and may eliminate the need for other more interventional drug application techniques, e.g., hypodermic injections, etc. Direct inhalation, can in some cases, allow smaller doses of a drug to be used to achieve the same desired results as the same drug taken orally. In other cases, inhalation can help to avoid undesirable side effects.

To provide for direct inhalation of a powdered drug, various dry powder inhalers have been used. These dry powder inhalers typically deliver dry powder from a bulk reservoir, capsule, or blister package, for inhalation by the patient. For sealing the powdered drug from the environment (to reduce caking, contamination, etc.), individual discrete sealed dose containers, such as blisters are preferred. However, while various blister dry powder storage and delivery devices have been used, disadvantages remain. For example, the blister must be strong enough to provide a good seal against the environment, but also be able to reliably release the drug powder when used by the patient. In addition, to better provide accurate doses, virtually of the drug powder must be released from the blister into the inhalation device, without, of course, allowing any of the blister or container material to mix with or flow out with the drug powder. As inhaled drugs, such as asthma drugs, may be used very frequently, the drug storage and delivery materials and device should advantageously be compact, low cost and easy to manufacture and use.

Accordingly, it is an object of the invention to provide an improved dry powder storage and delivery system, for use with an inhaler.

SUMMARY OF THE INVENTION

To these ends a dry powder storage and delivery device preferably includes a disk having radially spaced apart metal foil blisters containing a drug powder. The blisters are advantageously sealed onto an underlying metal foil shear layer. In the preferred embodiment, the shear layer is bonded onto a carrier disk. Shear tabs are advantageously bonded onto to the shear layer, underneath each blister, with a gap separating the tabs from the disk. In the preferred use, an actuator pushes on the tab, shearing or tearing out the shear layer from the blister, and releasing the dry powder contents of the blister.

The blister may also preferably be formed of a brittle material with a generally centrally located score line, so that the blister will burst open when engaged by an actuator, to release the powder drug contents of the blister.

BRIEF DESCRIPTION OF THE DRAWINGS

Other objects and features of the present invention will become apparent from the following detailed description taken together with the accompanying drawings. The drawings, however, are provided for illustration purposes only and are not intended as a limitation on the scope of the invention.

In the drawings, wherein similar reference characters denote similar elements throughout the several views.

DETAILED DESCRIPTION OF THE DRAWINGS

Figure 1:
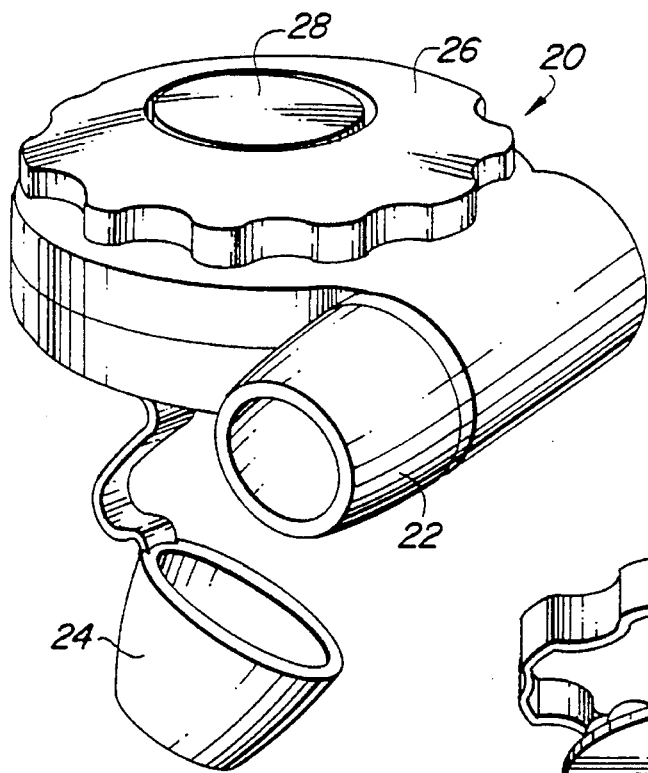
FIG. 1 is a perspective view of a dry powder inhaler.
Figure 1A:
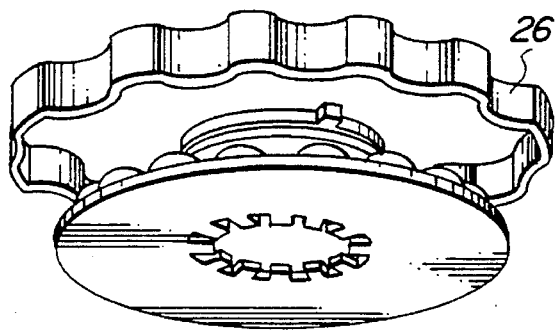
FIG. 1a is a perspective view of the advance knob of the inhaler of FIG. 1.
Figure 1B:
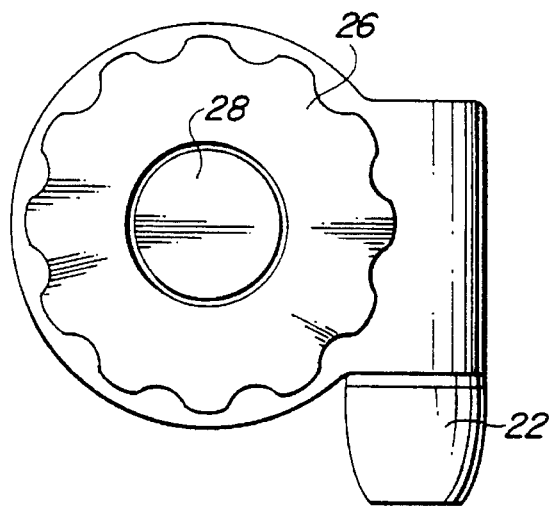
FIG. 1b is a plan view of the inhaler of FIG. 1.
Figure 1C:
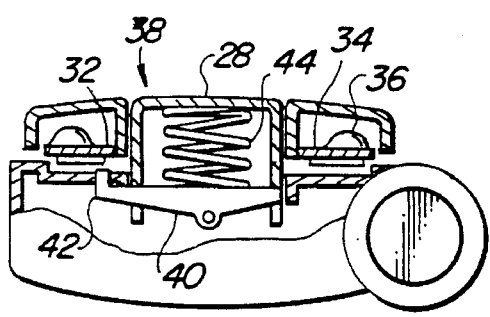
FIG. 1c is a schematically illustrated partial section view of the inhaler of FIG. 1.

Turning now in detail to the drawings, as shown in FIG. 1, a dry powder inhaler 20 has a mouthpiece 22 which is covered by a cap 24 when not in use. A knob 26 on top of the inhaler 20 may be used to advance individual drug doses for delivery through the mouthpiece 22. Referring to FIGS. 1, 1b, and 1c, a blister opening mechanism 38 includes a center button 28 positioned over a spring 44 on a rocker arm 40. The rocker arm 40 has a lever end 42 for pushing up on an interior tab 32 on a carrier disk 34 to shear or tear open a blister 36.

Figure 2:
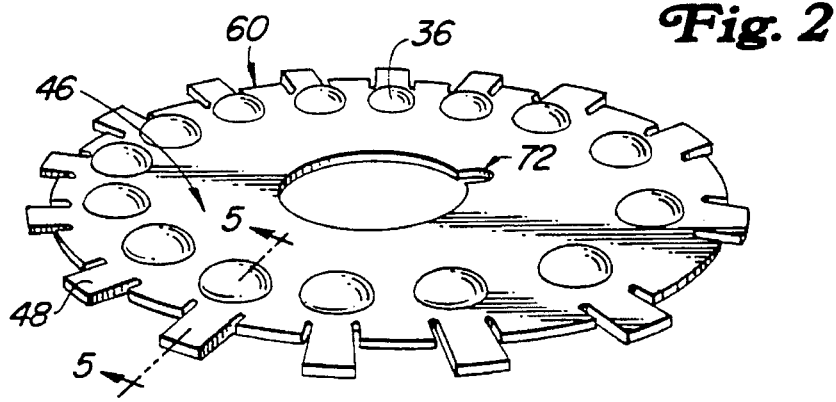
FIG. 2 is a perspective view of a drug carrier disk, having exterior tabs.
Figure 3:
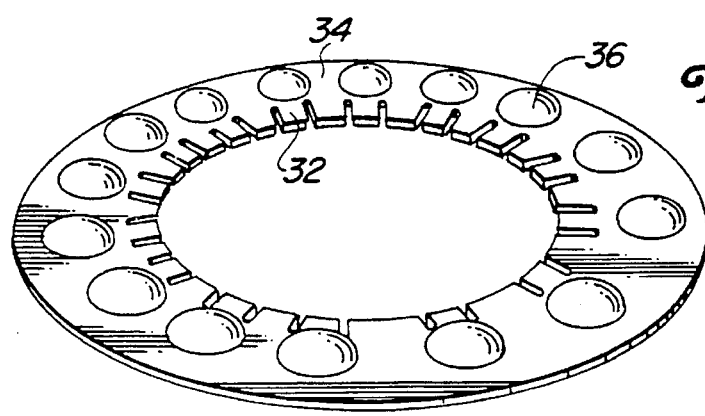
FIG. 3 is a perspective view of an alternative carrier disk, having interior disk tabs.
Figure 4:
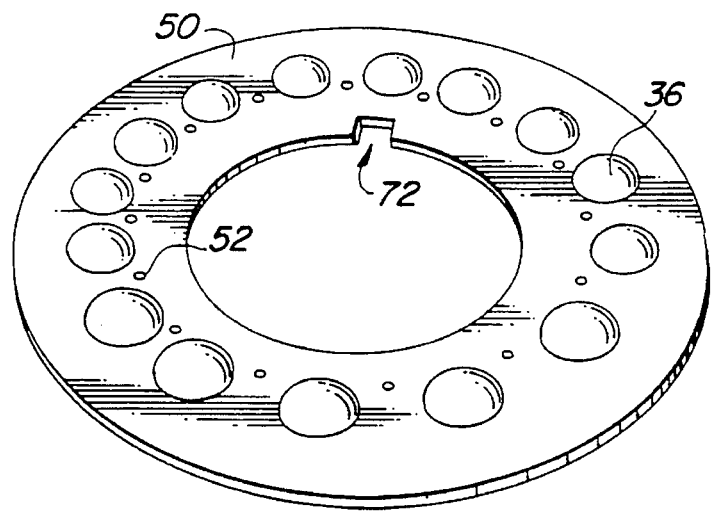
FIG. 4 is another disk carrier embodiment having tabs contained within the disk.

The carrier disk 34 and blister 36 are further illustrated in FIGS. 2–5. FIG. 2 shows a carrier disk 46 have exterior tabs 48 extending from radially spaced apart blisters 36 supported on a carrier disk 60. FIG. 3 better illustrates the carrier disk 34 shown in FIG. 1c, which has interior tabs 32. FIG. 4 shows another alternative carrier disk embodiment having tabs contained within the profile of the disk 50. Shear pin holes 52 extend through the disk 50, and in use, pins in an inhaler device extend through the holes 52 to push against a tab contained within the disk 50, to shear open the blisters 36. The carrier disks 34, 46 and 50 may include an indexing/drive notch 72.

Figure 5:
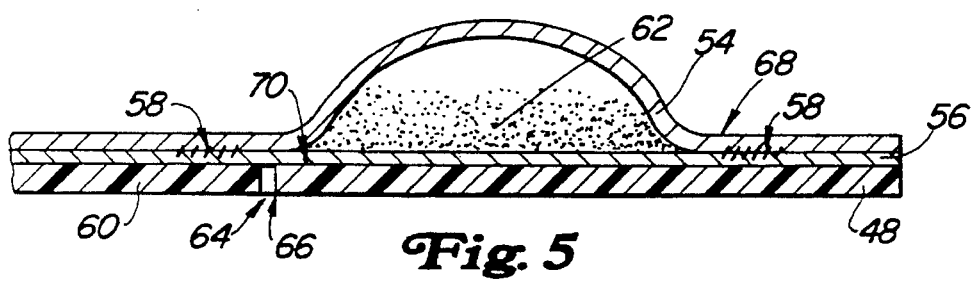
FIG. 5 is an enlarged partial section view taken along line 5—5 of FIG. 2.
Figure 5A:
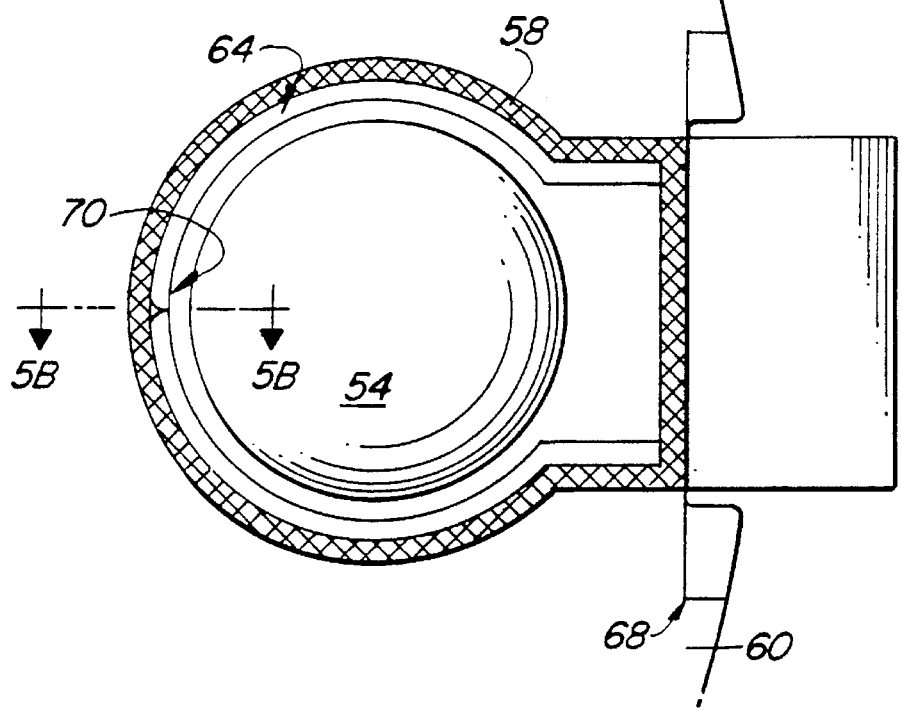
FIG. 5A is a top view thereof.
Figure 7:
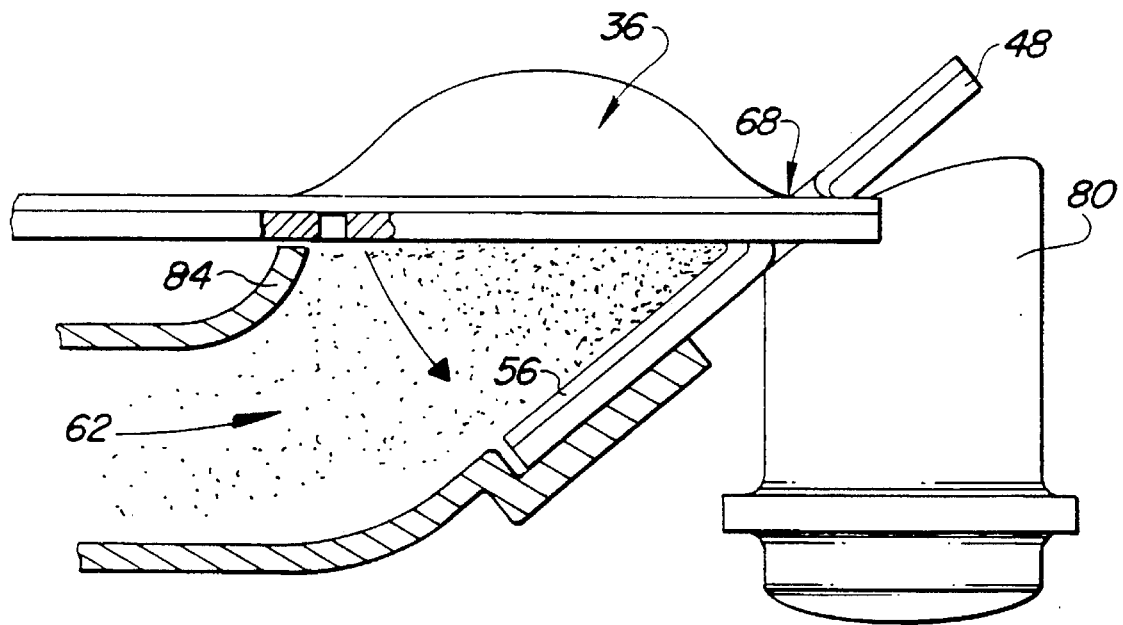
FIG. 7 is a side elevation view thereof, just after the blister has been sheared open.

Turning to FIG. 5 which illustrates an exterior tab carrier disk design, a blister shell 54 is positioned over a shear layer 56. The perimeter of the blister shell 54 is advantageously heat sealed to the shear layer 56 as shown at 58 in FIGS. 5 and 5a. Drug powder 62 is contained between the blister shell 54 and the shear layer 56. A tab 48 underlies the shear layer 56, below the blister shell 54. The tab is separated from the disk carrier 60 by a gap 64 all around, except for at the hinge line 68 (FIG. 7). The hinge line 68 may optionally be provided as an indented area. A stress concentrator 70, can similarly be included as an option by providing a point or tooth on the disk carrier 60 at the innermost location of the gap 64, just inside of where the blister shell and shear layer join. The stress concentrator can help start the shearing/tearing action of the shear layer.

Figure 5B:
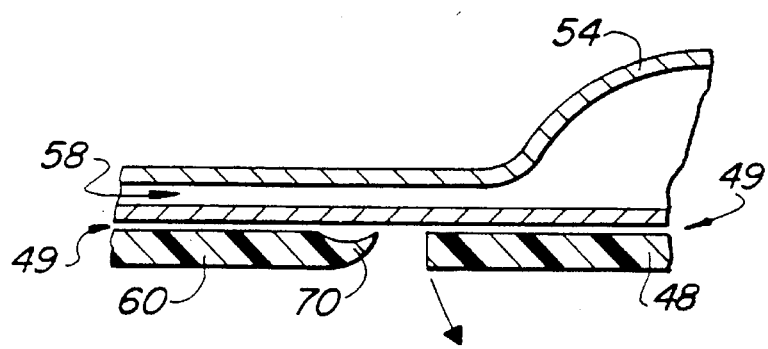
FIG. 5B is an exploded section view taken along line 5B—5B of FIG. A.
Figure 5C:
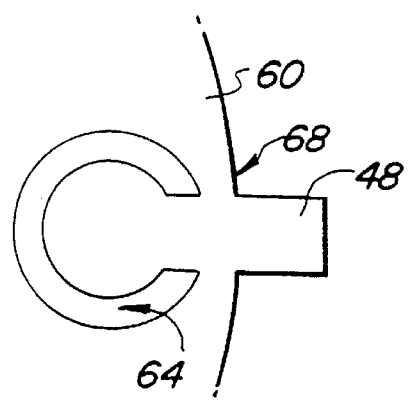
FIG. 5C is a bottom view thereof.

The blister shell 54 and shear layer 56 are preferably metal, e.g., aluminum, foils. The disk carrier 60 and tab 48 are preferably injection molded or die cut plastic. The shear layer 56 is adhered to the disk carrier 60 and tab 48 with an adhesive 49, and spans across the gap 64, as shown in FIGS. 5B and 5C.

Figure 6:
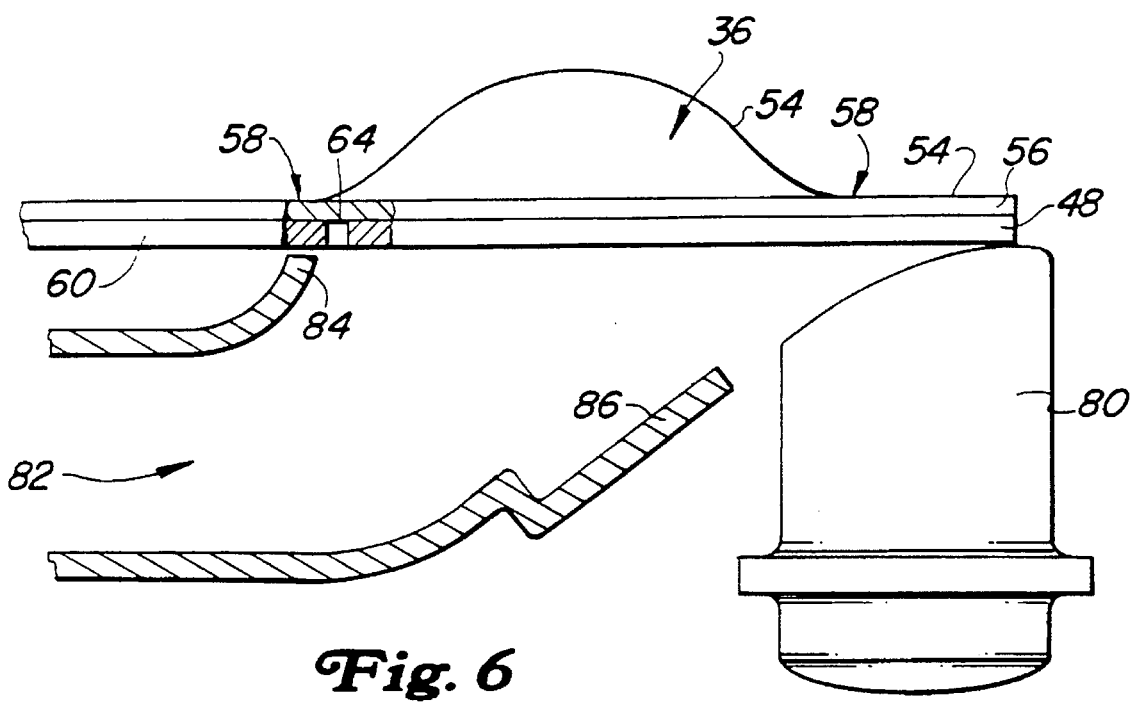
FIG. 6 is a side elevation view thereof, just prior to opening the blister.

FIGS. 6 and 7 illustrate operation of the disk carrier 60 within an inhaler. As shown in FIG. 6, the disk 60 rests on a support 84 positioned just inside of the gap 64. The blister 36 is positioned over a guide wall 86. As shown in FIGS. 6 and 7, an actuator 80 pushes up on the tab 48, which, acting as a lever, causes the shear layer 56 (which forms the bottom surface of the blister 36) to shear and tear away from the blister shell 54, thereby opening the blister. The powder 62 contained within the blister 36 falls free of the blister 36 and disk 60, into a chute in the inhaler. The tab 48 pivots about the hinge point 68. As this occurs, the heat seal 58 remains intact, with the opening of the blister 36 provided by the tearing of the shear layer 56.

Figure 8:
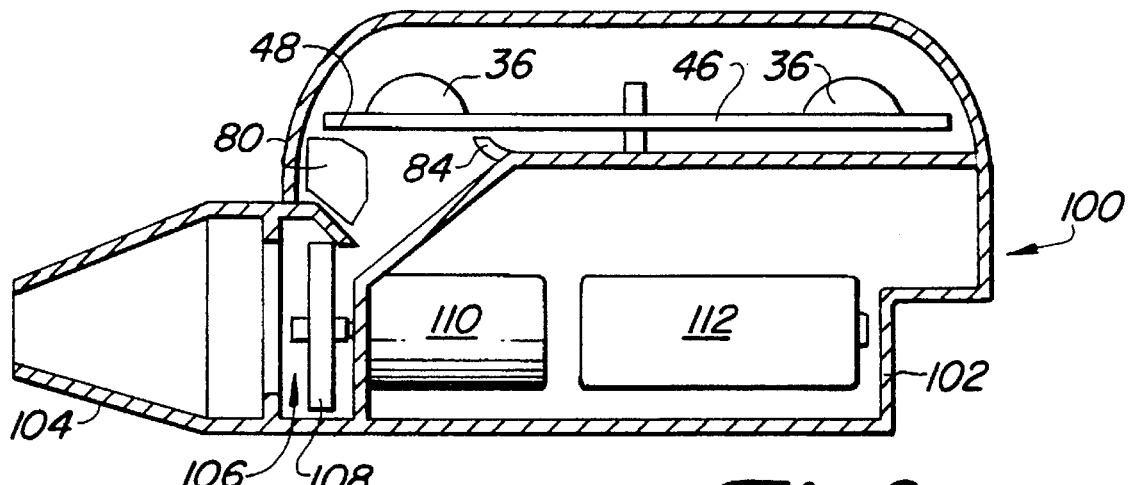
FIG. 8 is a section view of the carrier disk of FIG. 2 installed within a first embodiment of a dry powder inhaler.
Figure 9:
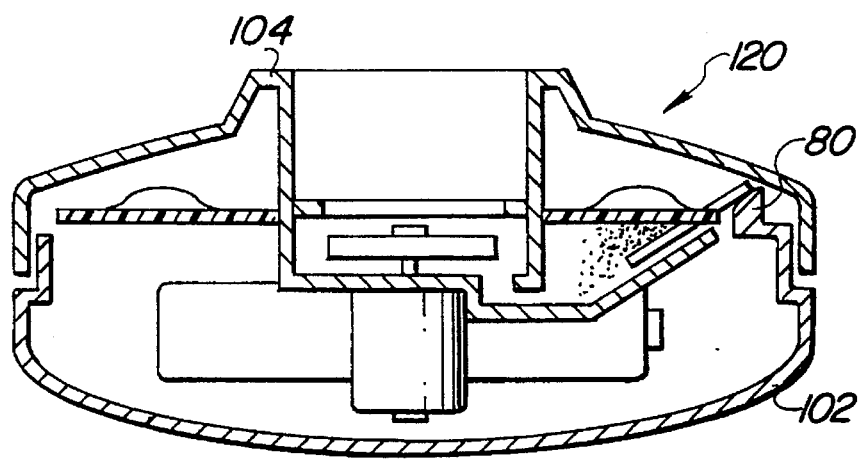
FIG. 9 is a section view of the disk carrier of FIG. 2 installed within a second embodiment dry powder inhaler.

Referring to FIG. 8, a dry powder inhaler 100 has a housing 102, a mouthpiece 104 and an impeller 108 within a mixing chamber 106. A motor 110 powered by batteries 112 spins the impeller 104. As the blister 36 is sheared open, as shown in FIGS. 6 and 7, the powder from the blister 36 falls into the mixing chamber 106, is mixed with air, and can be drawn out and inhaled by the patient. FIG. 9 shows an alternative inhaler embodiment having a centrally located mouthpiece 104.

Figure 10:
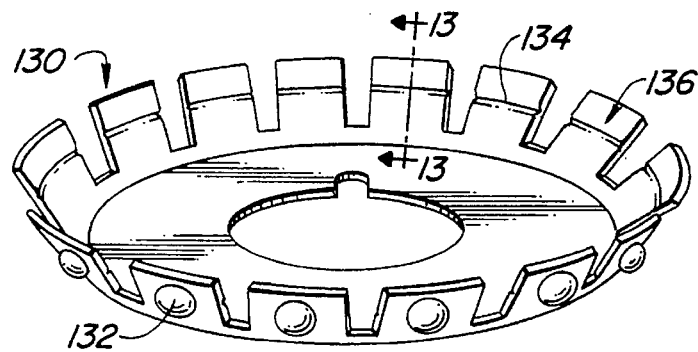
FIG. 10 is a perspective view of an alternative disk carrier having bursting circumferentially scored blisters on angled plates.

FIGS. 10–16 illustrate blisters which are burst open, rather than torn or sheared open. As shown in FIG. 10, a bursting blister carrier disk 130 has a plurality of bursting blisters 132 on angled plates 136. The plates 136 and blisters 132 have a circumferential score 134.

Figure 12:
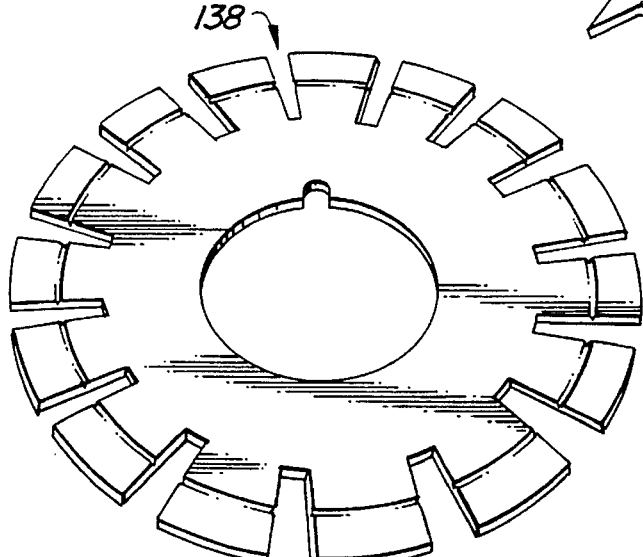
FIG. 12 is yet another disk carrier embodiment having circumferentially scored bursting blisters on flat plates.

FIG. 12 shows a similar embodiment, but with the plates flat in the plane of the disk rather than angled.

Figure 11:
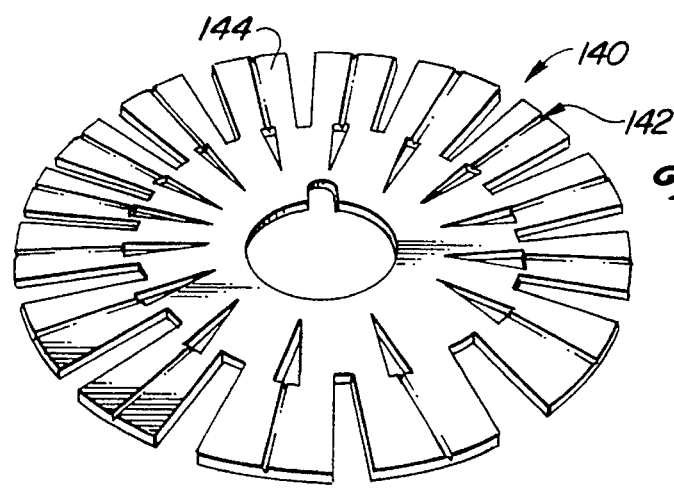
FIG. 11 is an alternative disk carrier embodiment having radially scored bursting blisters on flat plates.
Figure 11A:
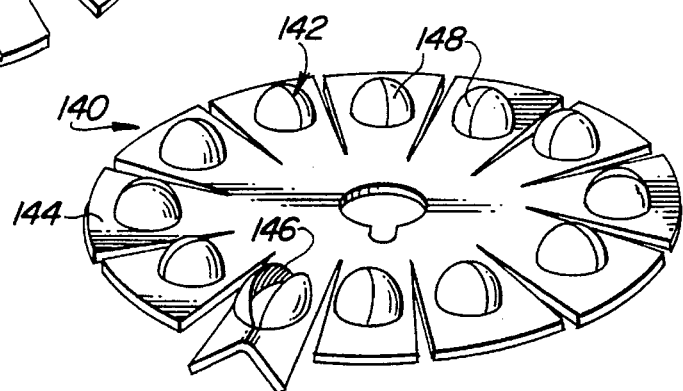
FIG. 11a a perspective view of the underside of the disk carrier of FIG. 11.

FIG. 11 shows an alternative embodiment having flat plates 144, with a radial score 142 on the plates 140 and blisters. FIG. 11a better illustrates the radial scored blisters 148 on the flat radially scored plates 144. The score or weakened section of the plates 144 and the blisters 142 are preferably centrally located on each blister 148.

Figure 13:
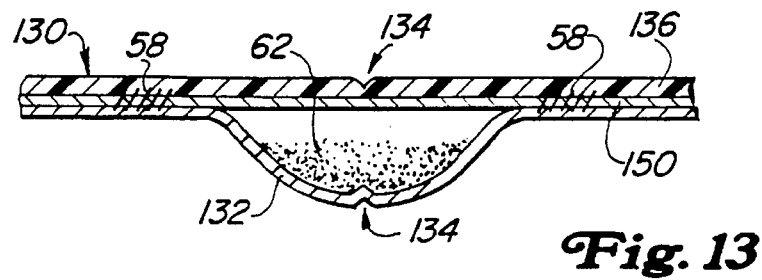
FIG. 13 is a section view fragment taken along line 13—13 of the FIG. 10.

As shown in FIG. 13, a bursting blister carrier disk 130 has a brittle blister shell 132 attached by a heat seal 58, at the blister shell perimeter, to a lid stock 150. The lid stock 150 in turn is bonded onto a plate 136. The blister shell 132 has a score or weak point 134 at its center. Correspondingly, the plate 136 has a score aligned with the score 134 on the blister shell 132.

The blister shell 132 is advantageously made from a brittle plastic or metal material. The lid stock 150 is preferably a metal (e.g., aluminum foil), while the plate 136 is preferably a hard injection molded or die cut plastic, as is the carrier disk center section.

Figure 14:
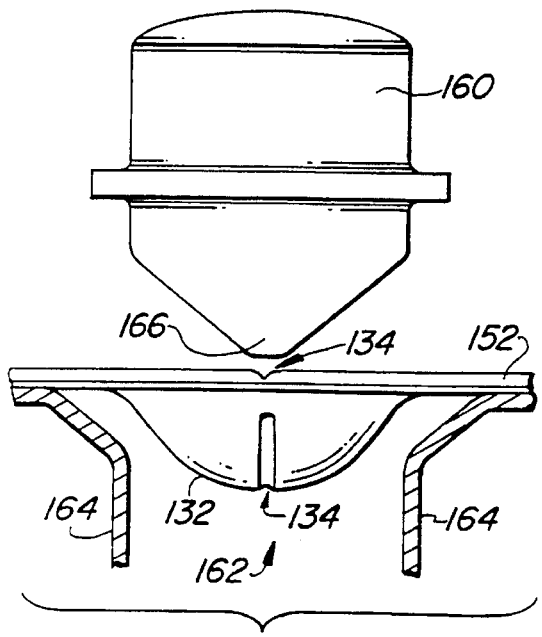
FIG. 14 is a side elevation view of the blister of FIG. 13, just prior to opening.
Figure 15:
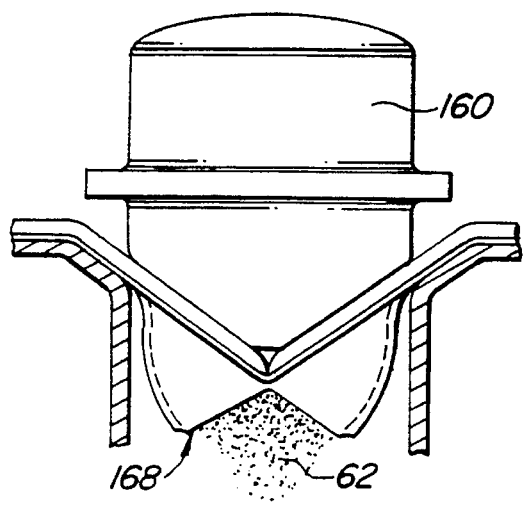
FIG. 15 is a side elevation view thereof, showing the blister immediately after opening.

In use, as shown in FIGS. 14 and 15, a plunger or actuator 160, having a broad flat blade shape with an angled point 166 is driven down onto the score 134 on the plate 136 which is supported at its sides by supports 164 (part of the inhaler). As the actuator is driven into the blister, the blister cracks or bursts open, as shown in FIG. 15, releasing the powder 62.

Figure 16:
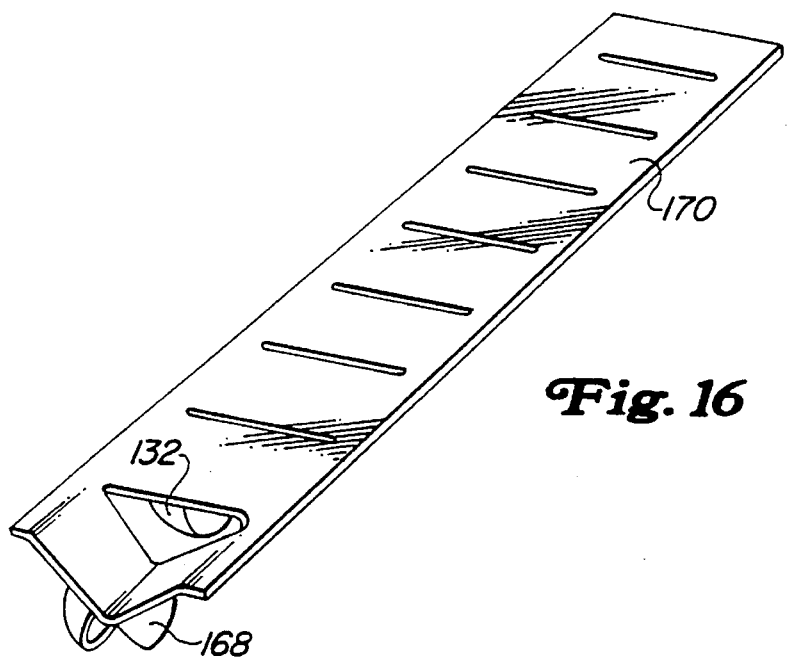
FIG. 16 is a perspective view of a straight strip carrier.

The blisters shown in FIGS. 5 and 13 may also be provided in a strip form, rather than a disk form, as shown in FIG. 16.

Thus, while several embodiments have been shown and described, it should be appreciated that many more modifications may be made, without departing from the spirit and scope of the present invention.

We claim:

1. A powder storage and delivery system for a dry powder inhaler, comprising:

a carrier;

a blister shell on the carrier;

a shear layer attached around the perimeter of the blister shell; and a tab pivotably attached to the carrier and attached to the shear layer.

2. The system of claim 1 wherein the carrier is a disk.

3. The system of claim 1 further comprising a plurality of blister shells and wherein the carrier is a strip.

4. The system of claim 1 wherein the shear layer comprises a single layer metal foil.

5. The system of claim 1 wherein the blister shell comprises a single layer metal foil.

6. The system of claim 1 wherein the blister shell extends over the carrier.

7. A powdered drug storage and delivery system comprising:

a carrier disk;

a tab attached to the carrier disk by a shear layer; and a blister containing a drug dose on the tab attached to the shear layer.

8. The system of claim 7 further comprising a gap separating the carrier disk from the tab on all sides, except at a hinge line bridging the gap.

9. A powdered drug storage and delivery system comprising:

a round carrier disk having a central opening;

a plurality of shear tabs radially projecting from the central opening, each shear tab having a circumferential edge spaced apart from the carrier disk across a gap, and with each shear tab pivotably connected to the carrier disk at a hinge line along one side of the tab;

a shear layer overlying, attached to, and connecting the carrier disc and the shear tabs; and a blister layer overlying and attached to the shear layer, the blister layer including a plurality of blister shells forming a powder containing space in between the shear layer and the blister shells, and with one blister shell formed on substantially each tab.

10. The powder drug storage and delivery system of claim 9 further comprising a stress concentrator at the circumferential edge of the tab, opposite from the hinge line.

11. The powder drug storage and delivery system of claim 9 further comprising a heat seal around a perimeter of substantially each blister shell, attaching the blister layer to the shear layer.

12. The system of claim 9 wherein the shear layer comprises a single layer metal foil.

13. The system of claim 12 wherein the metal foil is adhered to the carrier disk and shear tabs.

14. The system of claim 9 wherein the tabs extend inwardly towards the central opening.

15. A drug storage and delivery system comprising:
a carrier having a tab;
a shear layer having a top surface and a bottom surface, with the bottom surface of the shear layer attached to the tab;
a blister shell on the tab, with the blister shell having a perimeter attached to the top surface of the shear layer; and
a drug contained between the top surface of the shear layer and the blister shell.

16. The system of claim 15 wherein the carrier is a disk.

17. The system of claim 15 wherein the shear layer comprises a single layer metal foil.

18. The system of claim 15 wherein the blister shell comprises a single layer metal foil.

19. The dry powder delivery system, comprising:
a carrier disk;
a plurality of individual plates on the carrier disk radially spaced apart from each other;
a plurality of brittle blister shells, with substantially one blister shell attached to each plate;
each blister shell having a centrally located score line; and
a dose of powdered drug within the blister shells.

20. The dry powder delivery system of claim 19 wherein the score line is co-linear with a diameter chord of the disk.

21. The dry powder delivery system of claim 19 wherein the score line extends generally parallel to the perimeter of the carrier disc.

22. The dry powder delivery system of claim 19 wherein the plates are co-planer with the carrier disk.

23. The dry powder delivery system of claim 19 further comprising a score line on a plate aligned with the score line on a blister shell.

24. The dry powder delivery system of claim 19 further comprising a lidstock bonded on to the plates and a heat seal joining the blister shells to the lidstock.

25. A drug storage and delivery system comprising:
an inhaler having a housing;
an actuator displaceably mounted within the housing; and
a carrier disk incrementally rotatable on the housing, the carrier disk including a tab attached to the carrier disk by a shear layer and a blister on the tab attached to the shear layer;
with the actuator positioned to push on the tab and open the blister by shearing the shear layer.

26. A method of delivering a drug dose comprising the steps of:
providing an inhaler having a housing and a carrier disk with a tab and an actuator within the housing, said the carrier disk having a blister including a shear layer and containing a dose of drug;
advancing the carrier disk on the housing to a position in alignment with the actuator in the housing;
moving the actuator to engage and displace a tab on the carrier disk;
pivoting the tab via the actuator and shearing the shear layer sealing the dose of drug within the blister on the carrier disk; and
allowing the dose of drug to fall out of the blister and into the inhaler housing.

* * * * *